(12) United States Patent
Buessing et al.

(10) Patent No.: US 8,423,138 B2
(45) Date of Patent: Apr. 16, 2013

(54) IMPLANTABLE DEVICE FOR TRANSMITTING THERAPEUTIC AND DIAGNOSTIC SIGNALS

(75) Inventors: Heinrich Buessing, Berlin (DE); Ingo Weiss, Berlin (DE); Sami Sghaier, Berlin (DE)

(73) Assignee: Biotronik SE & Co. KG, Berlin (DE)

(*) Notice: Subject to any disclaimer, the term of this patent is extended or adjusted under 35 U.S.C. 154(b) by 0 days.

(21) Appl. No.: 13/309,398

(22) Filed: Dec. 1, 2011

(65) Prior Publication Data

US 2012/0158077 A1     Jun. 21, 2012

Related U.S. Application Data

(60) Provisional application No. 61/425,253, filed on Dec. 21, 2010.

(51) Int. Cl.
*A61N 1/08* (2006.01)
(52) U.S. Cl.
USPC ................................ 607/8; 607/60; 324/322
(58) Field of Classification Search .................. 607/8, 60
See application file for complete search history.

(56) References Cited

U.S. PATENT DOCUMENTS

2004/0124838 A1* 7/2004 Duerk et al. ................... 324/304
2004/0263172 A1* 12/2004 Gray et al. ..................... 324/322

OTHER PUBLICATIONS

European Search Report dated Mar. 27, 2012, 8 pages.

* cited by examiner

*Primary Examiner* — Christopher D Koharski
*Assistant Examiner* — Michael Carey
(74) *Attorney, Agent, or Firm* — ARC IP Law, PC; Joseph J. Mayo

(57) ABSTRACT

An implantable medical device configured to connect to function conductor(s) to transmit therapeutic signals or diagnostic signals or both. Includes a controllable voltage/current source or adjustable terminating impedance for the function conductor and a control unit that is connected to the voltage or current source or adjustable terminating impedance. The control unit controls a voltage, or a current to be applied to the function line, or to adjust the terminating impedance. Includes an interference field sensor connected to the control unit, and to detect an alternating electromagnetic or magnetic field, and to supply an output signal, upon detection. The control unit controls the voltage/current source as a function of the output signal of the interference field sensor, or sets the adjustable impedance so that a voltage induced as the result of an alternating electromagnetic or magnetic field is compensated for at the distal end of the electrode line.

11 Claims, 5 Drawing Sheets

IMPLANTABLE DEVICE FOR TRANSMITTING THERAPEUTIC AND DIAGNOSTIC SIGNALS

This application claims the benefit of U.S. Provisional Patent Application 61/425,253 filed on 21 Dec. 2010, the specification of which is hereby incorporated herein by reference.

BACKGROUND OF THE INVENTION

1. Field of the Invention

At least one embodiment of the invention relates to a permanently or temporarily implantable device having an elongated electrical conductor.

2. Description of the Related Art

Such devices, for example electrode lines for electrostimulation, have the disadvantage that their electrical conductor may heat up during magnetic resonance imaging due to the fact that the alternating magnetic fields that are present induce considerable electrical currents in the electrical conductor. In addition, such induced currents may be delivered to surrounding tissue via electrode poles of the electrode line, resulting in undesired heating of the tissue, for example. For this reason, there is presently little or no possibility for cardiac pacemaker patients to be tested using magnetic resonance imaging.

Implantable cardiac pacemakers or defibrillators (also jointly referred to below as cardiac stimulators or implantable pulse generators (IPG)) are typically connected to at least one stimulation electrode line, which at its proximal end which is provided for connection to the cardiac pacemaker or defibrillator has a standardized electrical terminal, and at its distal end which is provided for placement in the heart has one or more electrode poles. Such an electrode pole is used to deliver electrical pulses to the (myocardial) tissue of the heart or for sensing electrical fields in order to sense an activity of a heart. For these purposes, electrode poles typically form electrically conductive surface sections of an electrode line. Electrode poles are typically provided as an annular electrode in the form of a ring around the electrode line, or in the form of a point electrode or tip electrode at the distal end of the electrode line. At their proximal end the electrode poles are connected in an electrically conductive manner via one or more electrical conductors to contacts of the electrical terminal of the electrode line. Thus, the electrode lines at their proximal end extend between the contacts of the electrical terminal, and at the distal end one or more electrical conductors which electrically connect the one or more electrode poles to the one or more contacts extend between the electrode poles. These electrical conductors may be used on the one hand for transmitting stimulation pulses to the electrode poles, and on the other hand for transmitting electrical signals received via the electrode poles to the proximal end of the electrode line, and in the description below are also referred to in each case as a function line. Such function lines are electrical conductors which are necessary for the functions of the particular electrode line, and are thus subject to the risk of electrical currents being induced therein as the result of external alternating magnetic fields which, for example, may lead to undesired heating of the function lines or the electrode poles connected thereto, or may result in the discharge of corresponding currents via the electrode poles to surrounding tissue, and thus heating of the surrounding tissue.

BRIEF SUMMARY OF THE INVENTION

The object of at least one embodiment of the invention is to provide a device that eliminates the above-described problem.

According to at least one embodiment of the invention, this object is achieved by a device which is connected or is to be connected to at least one elongated electrical function conductor for transmitting therapeutic signals or diagnostic signals or both, and which has a controllable voltage source or current source (as a compensation signal generator) or an adjustable terminating impedance for the function conductor which is connected or is to be connected to the function conductor, and a control unit which is connected to the voltage source or current source or to the adjustable terminating impedance, and which is used to control a voltage to be applied to the function line by the voltage source, or to control a current to be applied to the function line by the current source, or to adjust the terminating impedance, and an interference field sensor which is connected to the control unit, and which is used to detect an alternating electromagnetic or magnetic field which may be present, and to supply an output signal, corresponding to a detected alternating electromagnetic or magnetic field, to the control unit.

The control unit is used to control the voltage source or current source as a function of the output signal of the interference field sensor with regard to a voltage or a current which is possibly to be applied to the function line, or to set the adjustable impedance in such a way that a voltage induced as the result of an alternating electromagnetic or magnetic field which may be present is compensated for at the distal end of the electrode line by superimposing a signal which is generated by the current source or voltage source, or which is reflected as a result of the adjustable impedance.

As the inventive principle, at least one embodiment of the invention encompasses the concept of actively or passively inducing an opposing signal at the proximal end in such a way that heating of the tip is partially or completely prevented.

Another inventive concept to be independently realized lies in placing at a distal end of an elongated implant, such as an electrode line, for example, a detector which returns a signal concerning voltage, current, or heating of the tip to the proximal end to optionally complete the control loop to compensate for the fields which are present at the tip.

For a device having an electrode line, it is preferred that the adjustable impedance or the voltage source is located at or near a proximal end of the electrode line.

A preferred adjustable terminating impedance includes a component by means of which a reactance may be adjusted, and a component by means of which an effective resistance may be adjusted. The component by means of which a reactance may be adjusted is preferably a capacitance diode. The component by means of which an effective resistance may be adjusted is preferably a PIN diode. A PIN diode is a diode with a wide intrinsic layer that is lightly doped between the P-type and N-type regions.

A preferred voltage source has a voltage-controlled oscillator.

The interference field sensor is preferably used to detect an output received at the proximal end of an electrode line.

Alternatively, the interference field sensor may be situated at the distal end of an electrode line, and may have a nonlinear component which in the event of current flow or applied voltage generates harmonic waves, which are then detected by a control unit at the proximal end of the electrode line and which may be evaluated for controlling the voltage source or the adjustable impedance. The nonlinear component may be a diode, for example.

According to one particularly preferred embodiment variant, the interference field sensor has a nonlinear component which generates harmonic waves in the event of current flow or applied voltage, and the control unit is used to set the adjustable terminating impedance or the voltage source in such a way that these harmonic waves disappear.

In addition to the embodiments described herein other alternative embodiments may include some or all of the disclosed features.

BRIEF DESCRIPTION OF THE DRAWINGS

At least one embodiment of the invention is explained in greater detail with reference to the figures, which show the following.

DETAILED DESCRIPTION OF THE INVENTION

The implantable cardiac stimulator 10 may be a cardiac pacemaker or a cardioverter/defibrillator (ICD). In the illustrated exemplary embodiment, the cardiac stimulator 10 is a ventricular cardiac pacemaker and defibrillator. Other known cardiac stimulators are dual-chamber cardiac pacemakers for stimulating the right atrium and the right ventricle, or biventricular cardiac pacemakers, which in addition to the right ventricle are also able to stimulate the left ventricle.

Such stimulators typically have a housing 12, which is generally made of metal and is therefore electrically conductive, and which may be used as a large-surface electrode pole. A connector housing 14, also referred to as a header, is typically affixed to the exterior of the housing 12. Such a header typically has contact sockets for accommodating plug contacts. The contact sockets have electrical contacts 16 which are connected via appropriate conductors to an electronics system situated in the housing 12 of the cardiac stimulator 10.

Figure 1:
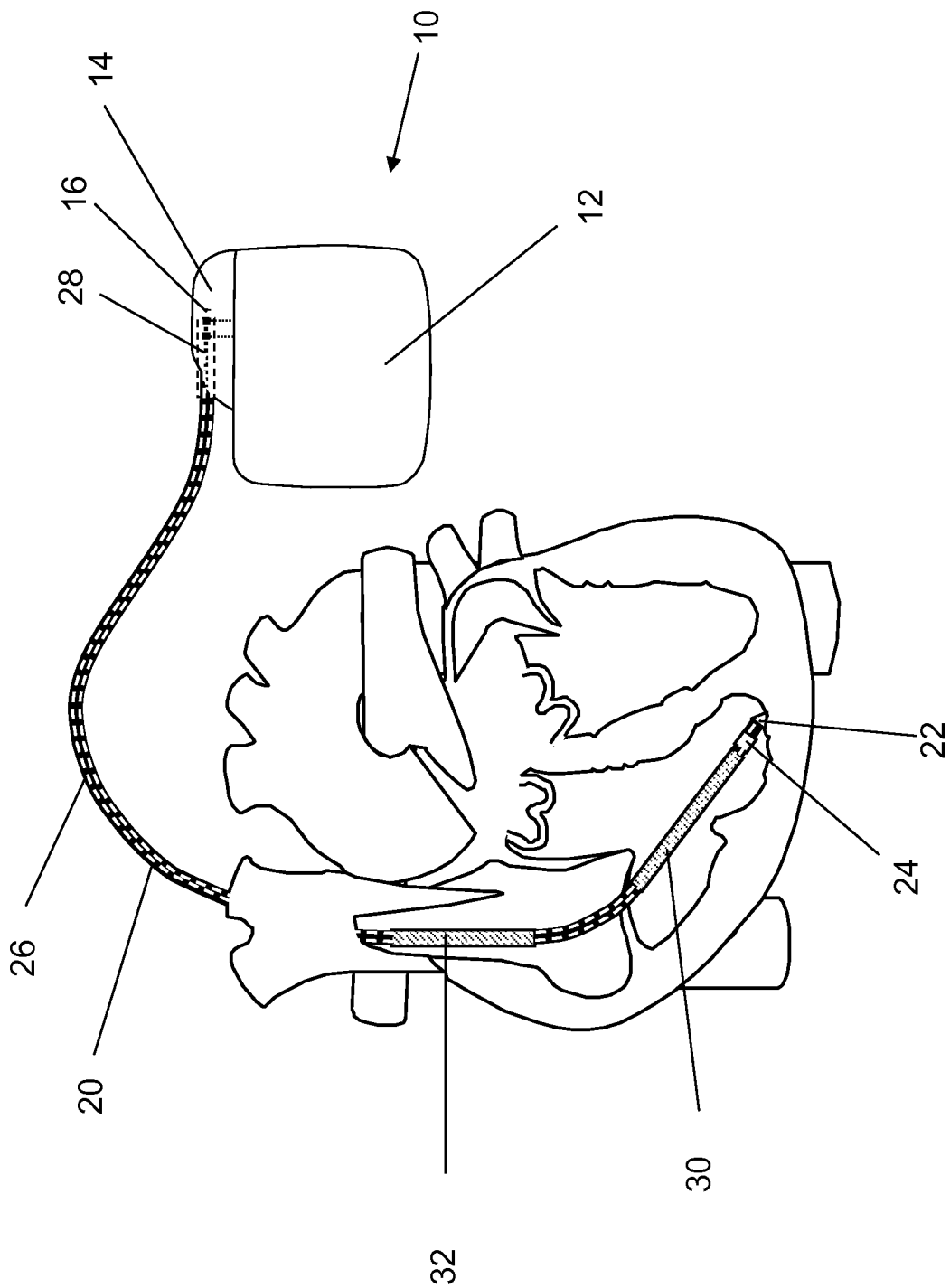
FIG. 1 shows as an implantable medical device an implantable cardiac stimulator 10 and an implantable electrode line 20 connected thereto.

The electrode line 20 likewise represents an implantable medical device within the meaning of at least one embodiment of the invention. Electrode poles in the form of a point electrode or tip electrode 22 and an annular electrode 24 present in the vicinity thereof are situated in a manner known per se at the distal end of the electrode line 20. The electrode poles 22 and 24 are designed in such a way that, depending on the function of a cardiac stimulator to which the electrode line 20 is connected, they are provided to sense electrical potentials of the cardiac tissue (myocardium) or to supply electrical signals, for example for delivering stimulation pulses to the cardiac tissue which surrounds them. FIG. 1 shows the manner in which the electrode poles, i.e., the tip electrode 22 and the annular electrode 24, and for the present application, the electrode line 20, are located in the apex of a right ventricle of a heart.

The tip electrode 22 and the annular electrode 24 are in each case electrically connected via at least one electrical conductor 26 to a plug contact 28 at the proximal end of the electrode line 20. The plug contact 28 has electrical contacts which correspond to the electrical contacts 16 of the contact socket in the connector housing 14 of the implantable cardiac stimulator. The electrical conductors 26 in the electrode line 20 may be designed as somewhat elongated cable conductors or as helically coiled conductors. Such conductors, which connect functional electrode poles to electrical contacts of the plug contact at the proximal end of the electrode line 20 in an electrically conductive manner, are referred to as function conductors within the scope of this description, since, for example, they transmit electrical signals used for the treatment from the plug contact to the particular electrode pole, or conduct sensed signals which represent electrical potentials from the particular electrode pole to the plug contact, and are thus used for the fundamental function of the medical device.

The electrical conductors 26 which connect the electrode poles 22 and 24 to the electrical contacts of the plug 28 of the electrode line 20 are enclosed over most of their length by an insulating sheath, resulting in targeted electrical contact with the tissue of the heart via the electrode poles.

In addition to the electrode poles 22 and 24, which are typically used for stimulation (in this case, ventricular) of the cardiac tissue, the electrode line 20 has two large-surface electrode poles 30 and 32, which are used as defibrillation electrodes and are formed by at least one bare helically wound wire.

At least one embodiment of the invention is explained with reference to a right ventricular cardiac pacemaker and defibrillator. As a medical device within the meaning of at least one embodiment of the invention, however, in principle an ablation electrode line may also be used, which in the application likewise extends into the heart of a patient and is controlled by a device located outside the patient, and for this purpose is connected to the device.

Figure 2:
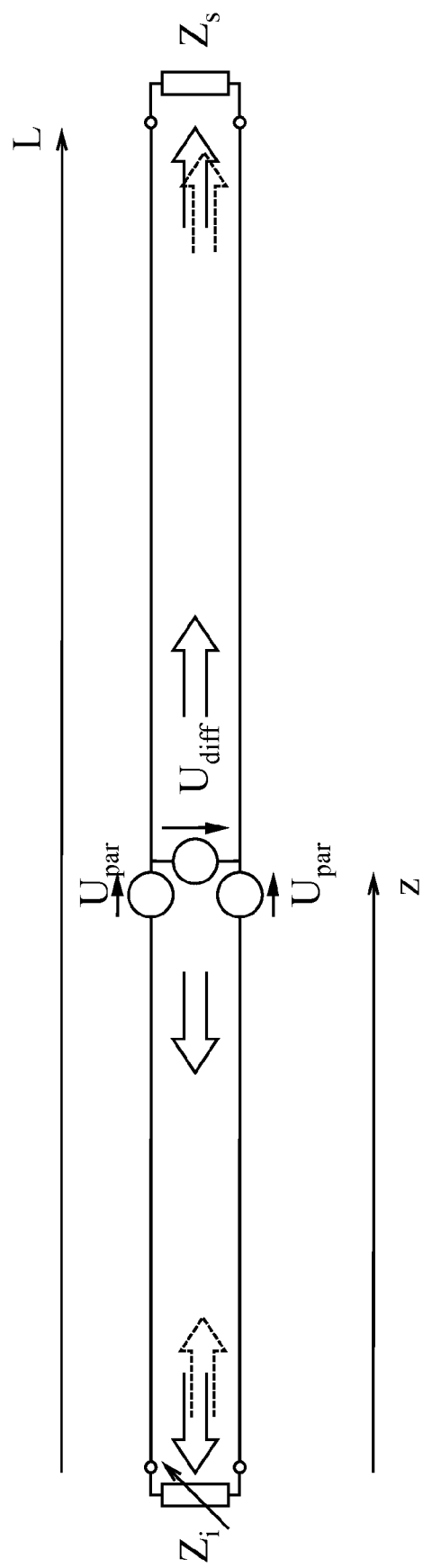
FIG. 2 shows an electrode line to which electrical voltages are supplied at various locations.

FIG. 2 illustrates the manner in which electrical voltages ($U_{par}$ or $U_{diff}$) are supplied to the electrode line at various locations z along an electrode line of length L by external electromagnetic fields, for example in MRI testing. This results in a current flow (wave propagation) along the electrode line toward the implant and also toward the distal end of the electrode line, also referred to below as the "tip." The current which is thus induced may result in excessive heating at the tip.

Since the voltage in the tip of the electrode is produced by the superimposition of voltages $U_{diff}$ and $U_{par}$ at various locations on the line, and depends on the phase, damping, and propagation speed (transmission function), the concept on which at least one embodiment of the invention is based is to compensate for the voltage at the electrode tip, i.e., at the distal end of the electrode line, by superimposing an additional signal in the electronic implant.

Figure 3:
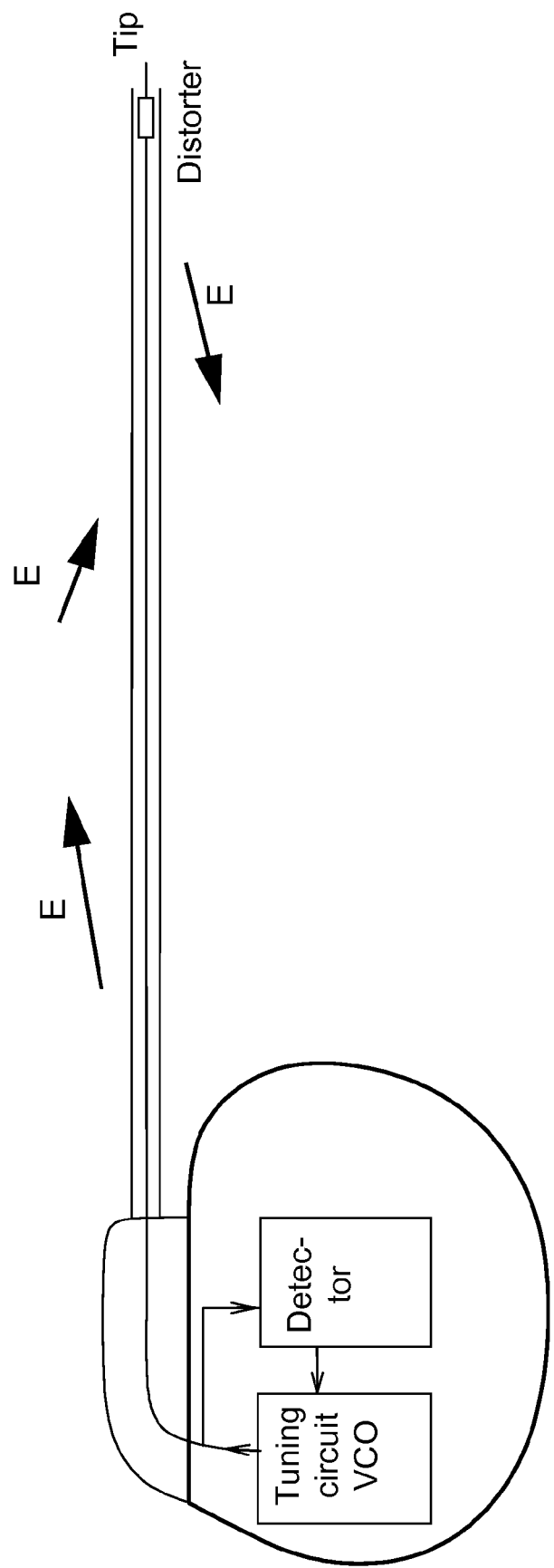
FIG. 3 shows an implantable medical device having an electrode line connected thereto, which at its proximal end has a controlled voltage source.

FIG. 2 illustrates the resistance of the implant as an adjustable resistor Zi, which reflects (dashed line arrow) the supplied signal ([solid line] arrow) in such a way that the signal is superimposed on the signal at the tip to produce a null result. This may also be achieved by a passive adjustable resistance (impedance) also via an adjustable voltage source, in particular a voltage-controlled oscillator (VCO) present at the proximal end, as illustrated in FIG. 3.

An interference field sensor is provided for supplying an output signal which represents a voltage, a current, or heating of the tip of the electrode line.

According to one embodiment variant, the interference field sensor is used to generate this signal from an output received at the proximal end of the electrode line. The interference field sensor is then, for example, integrated into the housing 12 of the cardiac stimulator 10.

In addition to detection of the received output at the proximal end, the resistor Zi or the oscillator may also be tuned according to the voltage or current in the tip, using a suitable detecting or transmitting component which then forms the interference field sensor. For example, a nonlinear component may be incorporated into the tip, and in the event of current flow or applied voltage transmits signals (in this example, harmonic waves) to the proximal end. The resistor or oscillator at the proximal end is then adjusted by a control loop, formed by the control unit, in such a way that these harmonic waves disappear. In this case, the particular detecting or transmitting component at the distal end of the electrode line forms the interference field sensor.

Figures 4A, 4B:
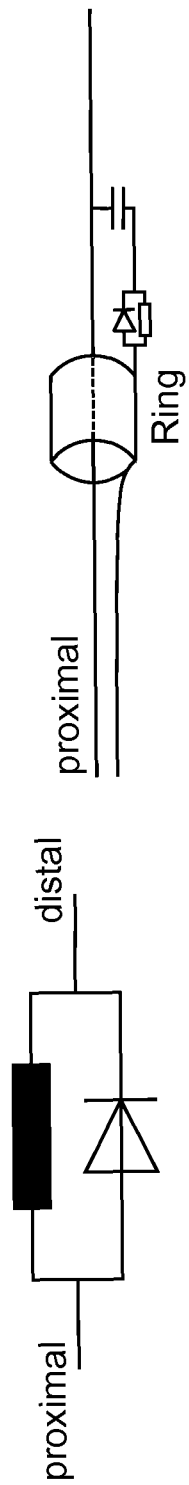
FIG. 4A shows an interference field sensor having a diode as a nonlinear component, which may also be situated at a distal end of an electrode line.
FIG. 4B shows one exemplary embodiment of an interference field sensor having a nonlinear component for an electrode line having multiple electrode poles.

FIG. 4A shows one possible design. In this case a diode as a nonlinear component is connected to a coil in the signal path, and is able to generate harmonic waves as a signal when current passes through the coil. The function of the coil is to counteract the generation of direct current voltage, thus maintaining the charge balance in the stimulation. FIG. 4B shows another exemplary embodiment having a nonlinear component for an electrode line having multiple electrode poles (tip and ring, for example).

Figure 5:
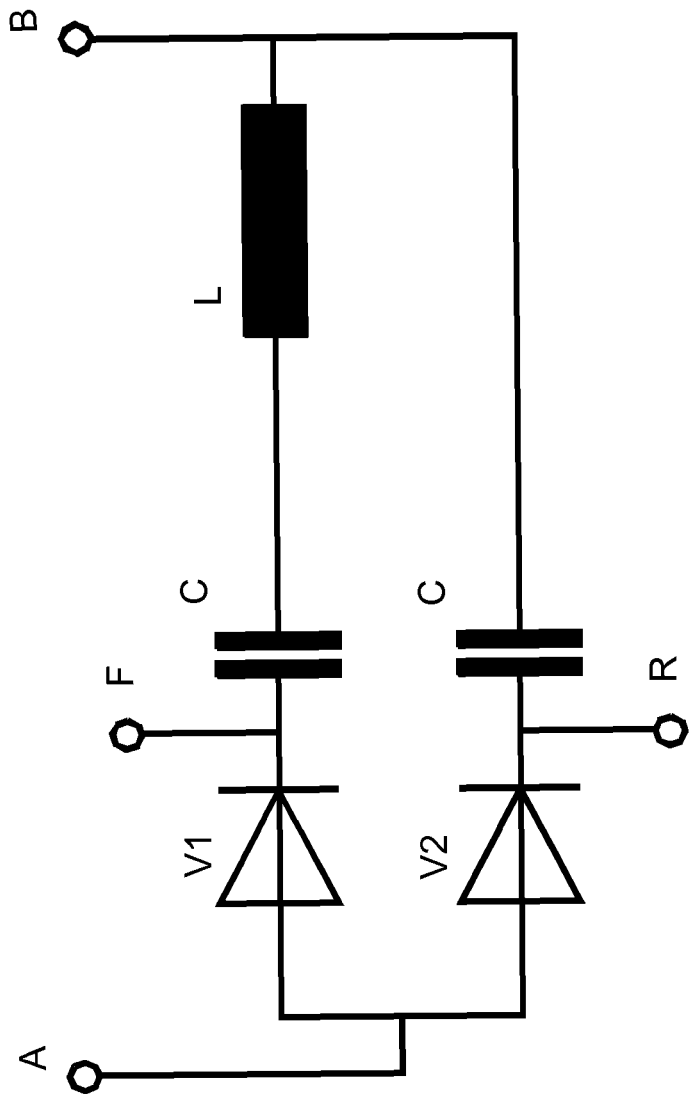
FIG. 5 shows one exemplary embodiment of an adjustable resistor Zi as adjustable impedance, which may be provided at the proximal end of an electrode line or in the housing of a cardiac stimulator.

FIG. 5 shows one exemplary embodiment of an adjustable resistor Zi as adjustable impedance between contacts A and B, which may be provided at the proximal end of the electrode line or in the housing of the cardiac stimulator. V1 is a capacitance diode (referred to as a varactor), so that the reactive component of Zi may be adjusted by setting the voltage at terminal F. V2 is a PIN diode, for example, so that the effective resistance of Zi may be adjusted by changing the voltage at terminal R.

This counteraction functions particularly well when the damping of waves on the electrode line is so slight that a large amount of energy is present at the proximal end, and a strong reaction of the proximal end to the distal end of the electrode line is expected.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device comprising:
   an implantable function conductor comprising at least one elongated electrical function conductor that is configured to transmit therapeutic signals or diagnostic signals or both;
   an implantable controllable voltage source or controllable current source or adjustable terminating impedance that is coupled to the function conductor;
   an implantable control unit which is connected to the controllable voltage source or controllable current source or to the adjustable terminating impedance, and which is configured to control a voltage to be applied to the function conductor by the controllable voltage source, or to control a current to be applied to the function conductor by the controllable current source, or to adjust an impedance of the adjustable terminating impedance;
   an implantable interference field sensor which is connected to the control unit, and which is used to detect an alternating electromagnetic or magnetic field, and to supply an output signal, corresponding to the detected alternating electromagnetic or magnetic field, to the control unit;
   wherein the implantable control unit is further configured to
   control the controllable voltage source or controllable current source as a function of the output signal of the interference field sensor and to vary the voltage or the current which is applied to the function conductor, or adjust the adjustable terminating impedance so that the voltage induced as a result of the alternating electromagnetic or magnetic field is compensated for at a distal end of the function conductor,
   wherein said voltage induced is compensated with a superimposed signal on the function conductor to produce a null result, wherein said superimposed signal is generated by the controllable current source or controllable voltage source, or which results from adjustment of the adjustable terminating impedance.

2. The implantable medical device according to claim 1, further comprising an implantable electrode line, wherein the adjustable terminating impedance or the controllable voltage source is located at or near a proximal end of the electrode line.

3. The implantable medical device according to claim 1, wherein the adjustable terminating impedance comprises a capacitance diode and a PIN diode.

4. The implantable medical device according to claim 1, wherein the implantable controllable voltage source comprises a voltage-controlled oscillator.

5. The implantable medical device according to claim 1, further comprising an implantable electrode line wherein the implantable interference field sensor is situated at a proximal end of the electrode line.

6. The implantable medical device according to claim 1, further comprising an implantable electrode line wherein the implantable interference field sensor is situated at a distal end of the electrode line and comprises a nonlinear component.

7. The implantable medical device according to claim 6, wherein the nonlinear component is a diode.

8. The implantable medical device according to claim 1, wherein the implantable interference field sensor comprises a nonlinear component configured to generate harmonic waves based on current flow or applied voltage, and wherein the control unit is configured to adjust the impedance of the adjustable terminating impedance or control the voltage of the controllable voltage source or control the current of the controllable current source so that the harmonic waves diminish.

9. The implantable medical device according to claim 6, wherein said nonlinear component is connected to a coil which is configured to counteract current flow or applied voltage, for maintaining charge balance.

10. The implantable medical device according to claim 8, wherein the control unit is configured to adjust the impedance of the adjustable terminating impedance or control the voltage of the controllable voltage source or control the current of the controllable current source by a control loop.

11. An implantable medical device comprising:
    an implantable function conductor comprising at least one elongated electrical function conductor that is configured to transmit therapeutic signals or diagnostic signals or both;
    an implantable controllable voltage source comprising a voltage-controlled oscillator that is coupled to the function conductor;

an implantable control unit which is connected to the controllable voltage source and which is configured to control a voltage to be applied to the function conductor by the controllable voltage source;

an implantable interference field sensor which is connected to the control unit, and which is used to detect an alternating electromagnetic or magnetic field, and to supply an output signal, corresponding to the detected alternating electromagnetic or magnetic field, to the control unit;

wherein the implantable control unit is further configured to control the controllable voltage source as a function of the output signal of the interference field sensor and to vary the voltage which is applied to the function conductor, so that the voltage induced as a result of the alternating electromagnetic or magnetic field is compensated for at a distal end of the function conductor, wherein said voltage induced is compensated with a superimposing signal on the function conductor to produce a null result, wherein said superimposed signal is generated by the controllable voltage source.

* * * * *